(12) United States Patent  
Bachelder

(10) Patent No.: US 7,927,311 B1
(45) Date of Patent: Apr. 19, 2011

(54) POST-SURGICAL DRAINAGE BULB SUPPORT SLING

(76) Inventor: Deborah Bachelder, Lake Jackson, TX (US)

( * ) Notice: Subject to any disclaimer, the term of this patent is extended or adjusted under 35 U.S.C. 154(b) by 369 days.

(21) Appl. No.: 11/999,829

(22) Filed: Dec. 5, 2007

Related U.S. Application Data

(60) Provisional application No. 60/872,885, filed on Dec. 5, 2006.

(51) Int. Cl.
| | |
|---|---|
| A61M 5/32 | (2006.01) |
| A61F 5/44 | (2006.01) |
| A61F 5/00 | (2006.01) |
| A45C 15/00 | (2006.01) |
| A45C 13/30 | (2006.01) |
| A45F 3/14 | (2006.01) |
| A45F 5/00 | (2006.01) |
| A45F 3/00 | (2006.01) |

(52) U.S. Cl. ........ 604/179; 604/345; 224/578; 224/257; 224/901.2; 224/148.4; 224/600; 224/602; 224/605; 602/4

(58) Field of Classification Search .................. 604/345; 602/4; 224/148.4, 578, 264, 901.2, 42.39, 224/651, 148.5–148.7, 600, 602, 605, 257, 224/265; D2/614
See application file for complete search history.

(56) References Cited

U.S. PATENT DOCUMENTS

| | | | | |
|---|---|---|---|---|
| 4,220,302 A * | 9/1980 | Hampton et al. | ............ | 248/102 |
| 4,337,938 A * | 7/1982 | Rodriguez | ............ | 482/74 |
| 4,341,331 A * | 7/1982 | McDougall | ............ | 224/219 |
| 4,498,613 A * | 2/1985 | Donahue et al. | ............ | 224/251 |
| 4,498,615 A * | 2/1985 | Johnson | ............ | 224/274 |
| 4,537,341 A * | 8/1985 | Kelly | ............ | 224/620 |
| 4,858,801 A * | 8/1989 | Sameniego | ............ | 224/264 |
| 4,911,347 A * | 3/1990 | Wilhite | ............ | 224/257 |
| 4,978,044 A * | 12/1990 | Silver | ............ | 224/601 |
| 5,205,832 A * | 4/1993 | Tuman | ............ | 604/179 |
| 5,332,137 A * | 7/1994 | Violette | ............ | 224/257 |
| 5,664,581 A * | 9/1997 | Ashley | ............ | 128/876 |
| 5,722,573 A * | 3/1998 | Carnel | ............ | 224/148.2 |
| 6,006,970 A * | 12/1999 | Piatt | ............ | 224/257 |
| 6,371,346 B1 * | 4/2002 | Sharma | ............ | 224/578 |
| 6,610,032 B1 * | 8/2003 | Prody | ............ | 604/179 |
| 6,979,303 B2 * | 12/2005 | Jestrabek-Hart | ............ | 602/4 |
| 7,048,160 B2 * | 5/2006 | Anderson | ............ | 224/148.6 |
| 2004/0144820 A1 * | 7/2004 | Herold | ............ | 224/605 |
| 2008/0296325 A1 * | 12/2008 | Tepper | ............ | 224/148.6 |
| 2009/0062705 A1 * | 3/2009 | Toso | ............ | 602/19 |

* cited by examiner

Primary Examiner — Tatyana Zalukaeva
Assistant Examiner — Susan Su
(74) Attorney, Agent, or Firm — Kenneth A. Roddy

(57) ABSTRACT

A lightweight comfortable support sling formed of soft flexible fabric material is supported around the back of the neck of postoperative patients in an inverted U-shaped configuration with the opposed ends of the sling hanging down along the front or sides of the patient's torso. Multiple conventional post-surgical fluid drainage receptacles can be secured at each end of the sling by hook and loop fasteners and adjustably positioned at locations adjacent to the body of the wearer to allow easy access and avoid tangling and stress on the drain tubes. While still having the drainage receptacles attached, the sling can be separated in the middle and easily removed from the patient's neck to relieve pressure, then re-fastened for ambulation. The sling is capable of supporting ten or more drainage bulbs.

4 Claims, 5 Drawing Sheets

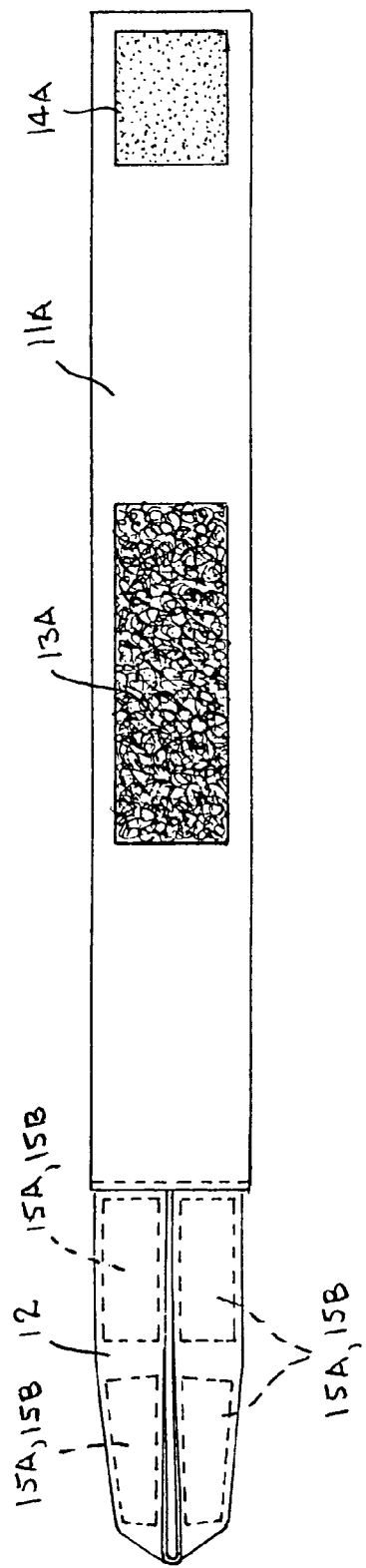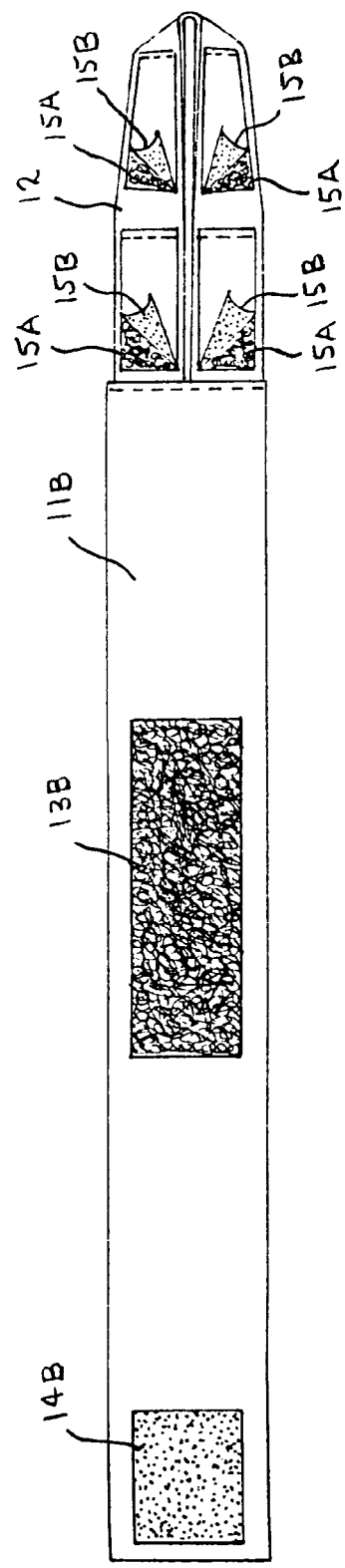
Fig. 2
Fig. 3

POST-SURGICAL DRAINAGE BULB SUPPORT SLING

CROSS REFERENCE TO RELATED APPLICATION

This application claims priority of U.S. Provisional Patent Application Ser. No. 60/872,885, filed Dec. 5, 2006.

BACKGROUND OF THE INVENTION

1. Field of the Invention

This invention relates generally to surgical drainage support devices, and more particularly to a neck sling to be worn by a postoperative patient for supporting one or more post-surgical fluid drainage collection reservoir bulbs or other medical devices.

2. Background Art

Following certain types of surgery, especially surgery involving the removal of tissue, the resulting body cavity may fill with fluid. Examples of such surgery include mastectomies and lumpectomies with auxiliary nodal dissection, which involved removal of lymph nodes under the arm. To relieve swelling and infection that may occur if the fluid is left in the body, one end of a drainage tube, which may be two feet long or longer, is inserted through the surgical incision into the cavity and is normally sutured, or stitched directly to the skin at the surgery site, and the other end of the drainage tube is attached to a post-surgical fluid drainage bulb or plastic bottle receptacle for collecting the fluid. Such drainage bulbs, also known as bulb drains or suction reservoirs, are capable of creating a negative pressure in the body cavity to facilitate drainage and hold the skin against the muscle until it heals. Some postoperative procedures require multiple tubes and drainage bulbs. Depending on the surgery and the amount of fluid buildup expected, the number of drainage tubes and receptacles utilized can vary from as few as one to many. However, when many drainage tubes are utilized, the managing of the tubes and their associated receptacles pose certain problems. In the past, it was common to pin the receptacles to the clothing or gown worn by the patient or to the bandage for the incision itself.

While not very comfortable, this procedure is somewhat effective in the hospital where an open gown was worn, thereby easing the ability of the patient to accommodate basic bodily functions. Furthermore, the awkwardness and discomfort is increased with multiple sets of bottles and tubes. In addition, outside of the hospital, where patients wear standard, relatively constricting clothes, it is not practicable to use such means to support drain bulbs. With the advent of insurance company mandates on shorter hospital stays for many types of surgeries, the problems associated with supporting drain bulbs have become more prevalent.

It is not uncommon for a postoperative patient to come home with four or more suction reservoir bulbs pinned to their clothing or post surgical dressings. For example, the plastic tabs or loops of the drain bulbs may be pinned directly to a wide elastic band wrapped around the patient's chest. In order to shower, this patient must first unpin the bulbs and then remove the elastic band. At this point there is nothing to attach the bulbs to and the patient or an assistant may be required to hold the bulbs and tubes in their hands while the patient attempts to shower, which is extremely cumbersome and runs the risk of dropping the bulbs.

Others have attempted to overcome these problems by providing belts or harnesses that encircle the chest area or the waist of a postoperative patient to support fluid drainage receptacles. While these devices may resolve some of the problems associated with supporting post operative drainage receptacle, they are not particularly comfortable after being worn for extended periods of time, can irritate the skin, and due to their structure cannot effectively support a plurality of drainage bulbs at locations adjacent to the body of the wearer to allow easy access and avoid tangling of the drainage tubes.

Turner, U.S. Pat. No. 5,643,233 discloses a post-surgical drainage carrier for carrying a post-surgical drainage container used for draining fluids from patients after surgery. The post-surgical drainage carrier includes a pouch and a belt. The pouch includes a front pouch sidewall and a back pouch sidewall. The front pouch sidewall terminates at a pouch lip which is interconnected with a pouch extension at first and second lip attachment points which may extend downwardly and inwardly to open a pouch mouth for placing the drainage container within the pouch interior.

Watson et al, U.S. Pat. No. 6,152,915 discloses a drain tube belt and shower pack kit. The drain tube belt is a strap that fits around the abdomen and has a pouch pocket for receiving the drain tube and the collection bulb. The kit also includes a separate second receptacle for holding the collection bulb by itself. The second receptacle is a bag-like pouch formed of mesh for receiving the collection bulb and has a loop handle at the open top end which can be held by the patient, or the handle may be attached to a shower curtain rod or hung on a plumbing fixture such as a faucet.

Ekey, U.S. Pat. No. 6,270,485 discloses a post surgical drainage receptacle support system that includes an adjustable belt and a plurality of pouches for individually receiving a drainage receptacle. A loop is provided on the back of the pouch for slidably receiving the belt, so that the pouch may be positioned directly underneath or directly above an insertion point for the drainage tubes.

Russo, U.S. Pat. No. 6,296,164 discloses a medical device holder that includes a strap for attachment to a patient, and one or more pouches attached to the strap, each pouch including a front layer and a back layer that forms a pocket for receiving a medical device such as a drainage bulb or feeding tube, and a first fastener fixedly attached to an inner surface of the front layer to attach the front layer to the back layer to secure the medical device in the pouch.

Ruess, U.S. Pat. No. 6,511,467 discloses a bib-like drainage reservoir garment having a front panel with an interior and exterior surface, and may have a back panel adjoined at a shoulder line to the front panel, and has a head/neck aperture positioned on or adjacent to the shoulder line, and a plurality of pockets attached to the interior surface of at least one of the front panel and the back panel for holding drainage reservoir bulbs.

Hadley-Fruit, U.S. Pat. No. 6,524,288 discloses a drainage reservoir support assembly that includes at least one generally cylindrical cup-like container having an open top end for receiving and containing the reservoir of a medical drainage device. A strap is provided for removably supporting the container from the neck of a user. The strap includes a first end and a second end with each of the ends of the strap being mounted on a peripheral wall of the container such that the strap forms a loop.

Prody, U.S. Pat. No. 6,610,032 discloses a surgical drainage apparatus that includes a belt which extends about the waist of a patient and is secured at a selected tightness thereon, the securing device being adjustable as to tightness. An outside surface of the belt has plural spaced apart elongate hook and loop fasteners aligned with a longitudinal axis of the belt, each of the fasteners comprising a first attachment element integral with the outside surface of the belt, and a second attachment element permanently fastened at one end of the first attachment element for receiving a fluid storing bulb having an inlet nipple adapted for receiving a fluid conduit for conducting a bodily fluid into the bulb, and an outlet nipple adapted for expulsing the fluid collected. A stopper, temporarily seals the outlet nipple when it is not in use. An attachment band provides a loop adapted for receiving one of the second attachment elements for engaging the fluid storing bulb with the belt within reach of a person wearing the belt. A fluid conduit engages the inlet nipple of the fluid storing bulb at one end, and at the other end, the source of the bodily fluid.

Urbina et al, U.S. Published Patent Application 20060173427 discloses a post operative breast surgery drain support garment including a form fitting vest-like support structure and one or more pouches attached to the front of the support structure, each of which is adapted in size and shape so as to form fittingly receive and maintain therein a single drainage receptacle. A drainage tube passes through drainage tube openings defined in the garment and retaining members are releasably mounted to the support structure and extend across at least a portion of the drainage tube openings to retain the drainage tube against the body thereby minimizing uncomfortable tugging.

The present invention overcomes the aforementioned problems, and is distinguished over the prior art devices, by a lightweight comfortable support sling which is supported around the back of the neck and shoulders of postoperative patients that supports one or multiple drainage bulbs or receptacles at locations adjacent to the body of the wearer to allow easy access and avoid tangling and stress on the drain tubes, and which can be worn under clothing. The sling is adjustable in length and, while still having the drainage bulbs attached, can be separated in the middle and easily removed from the patient's neck to relieve pressure, then re-fastened for ambulation. The sling is capable of supporting ten or more drainage bulbs.

BRIEF DESCRIPTION OF THE DRAWINGS

FIG. 2 is a perspective view of the first and second elongate rectangular straps that are assembled together to form the neck sling.

FIGS. 3 and 4 are perspective views showing the loop with hook and loop fasteners at the end of the first and second elongate rectangular straps.

DESCRIPTION OF THE PREFERRED EMBODIMENT

Referring to FIGS. 1-5, there is shown a preferred neck sling 10 for supporting one or more drainage bulbs B adjacent to the body of a postoperative patient, shown in an assembled condition. The neck sling 10 includes a first and second elongate rectangular strap 11A and 11B, each formed of a soft flexible fabric material. A loop 12 formed of a soft flexible fabric material is secured to one end of each strap, respectively. In a preferred embodiment, the straps 11A, 11B are approximately 36" in length and 3" wide, and the loops 12 are approximately 1½" wide and form a loop that extends approximately 8" beyond the end of the strap. In a preferred embodiment, but not limited thereto, the straps and loops are formed of a soft, machine washable material, such as 100% cotton flannel material.

A longer strip 13A and a shorter strip 14A of one element of a hook and loop fastener material are secured to one side of one elongate strap 11A in longitudinally spaced relation, and a longer strip 13B and a shorter strip 14B of the mating element of the hook and loop fastener material are secured to one side of the other elongate strap 11B in longitudinally spaced relation. A plurality of shorter strips 15A of the loop element of hook and loop fastener material are secured to one side of each loop, and the mating strips 15B of the hook element of the hook and loop fastener material are secured at one end to one end of a respective strip of the loop element, so as to be unfastened by lifting one end.

In a preferred embodiment, the longer pair of strips of the loop member of the hook and loop fastener on the first strap are each approximately 2" wide and 20" long; the shorter pair of strips of the hook fastener on the second strap are each approximately 2" wide and 4" long; and each mating pair of the shorter strips 15A, 15B of the hook and loop fasteners on the loops 12 are approximately 1" wide and 3" long. In a preferred embodiment, but not limited thereto, there are four mating pairs of the shorter strips of the hook and loop fasteners 15A, 15B on each of the loops.

Figure 1:
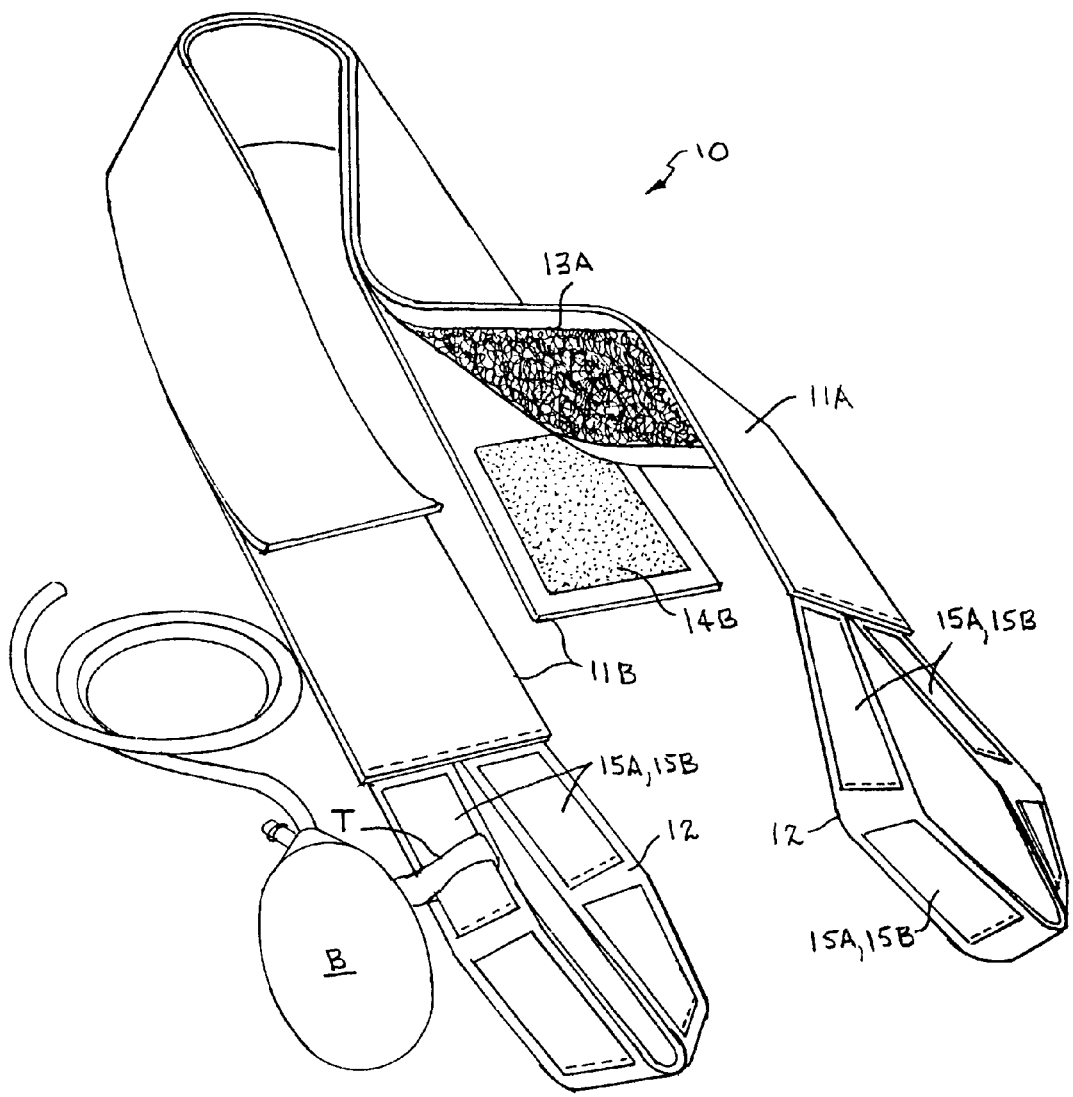
FIG. 1 is a perspective view of the neck sling for supporting one or more drainage bulbs adjacent to the body of a postoperative patient, in accordance with the present invention.
Figure 4:
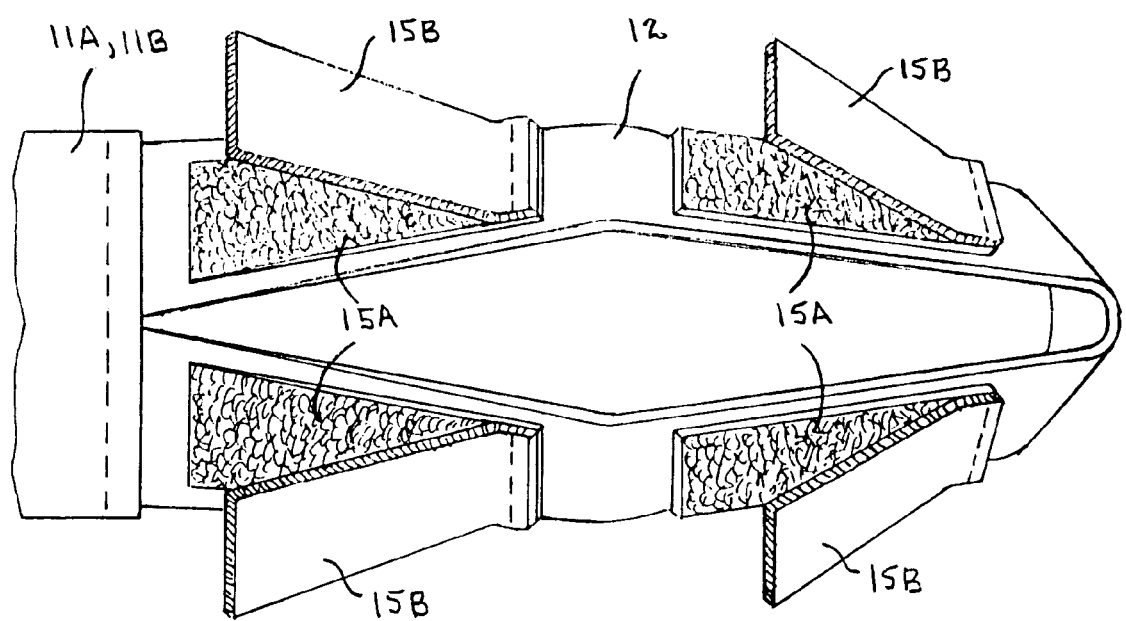
Figure 5:
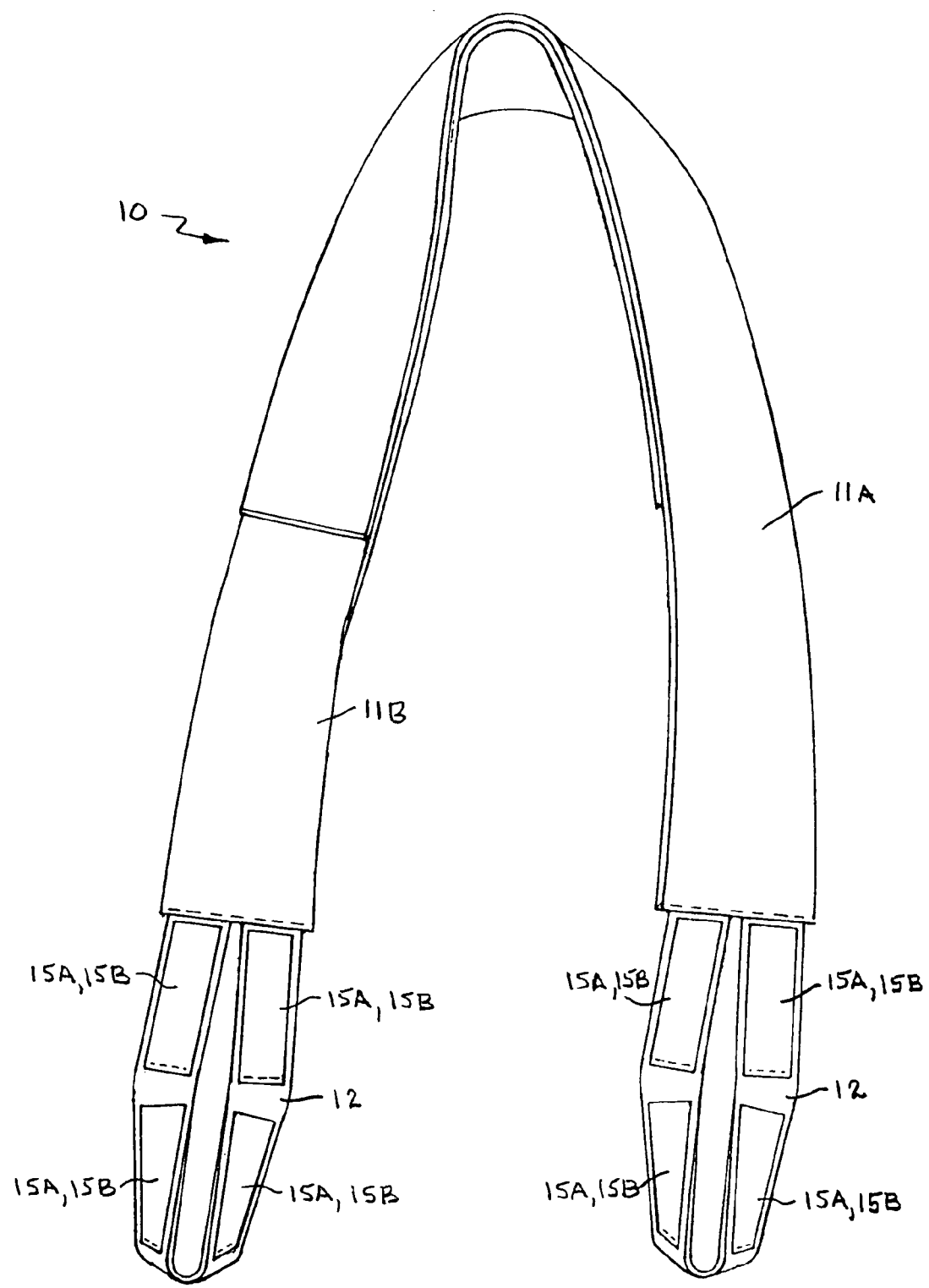
FIG. 5 is a perspective view showing the first and second elongate rectangular straps assembled together to form the neck sling.
Figure 6:
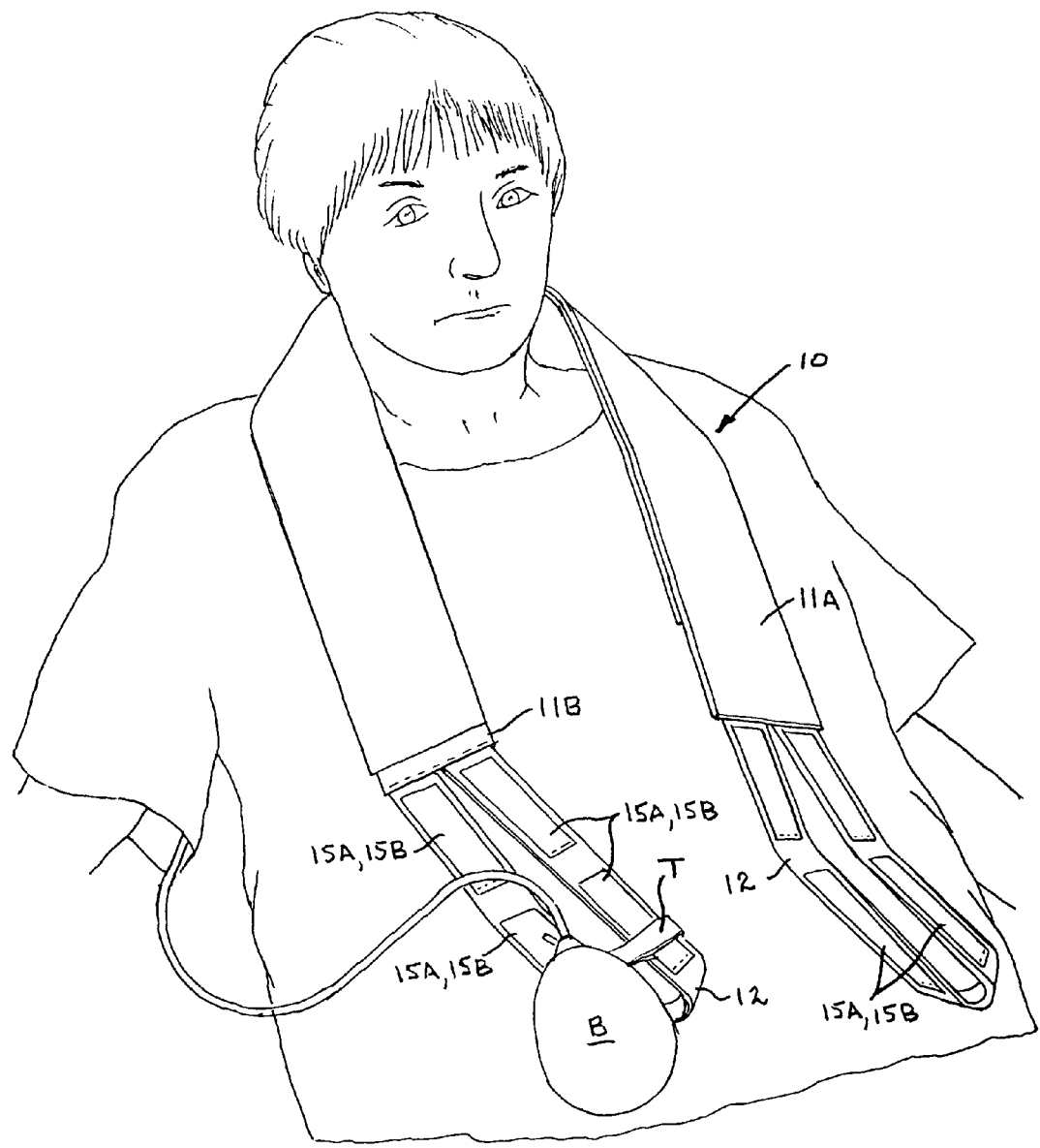
FIG. 6 is a perspective view of the neck sling being worn by a patient and supporting a drainage bulbs adjacent to the body of the patient.

The sling 10 is assembled by overlapping the first and second elongate rectangular straps 11A, 11B with their respective hook and loop fasteners 13A, 13B, 14A and 14B in face-to-face relation and pressing them together to engage the fasteners. The elongate rectangular straps 11A, 11B may be overlapped and releasably fastened together in adjustable longitudinally spaced relation relative to one another, so as to achieve a desired total length. As best seen in FIGS. 1 and 6, one or more conventional post-surgical fluid drainage bulbs B can secured to the loops 12 at each end of the sling by lifting one end of the appropriate hook member 15B of the hook and loop fastener on the loop and slipping it through the conventional tab T of the drainage bulb B and then pressing it down to engage the fastener and secure the bulb to the loop.

As seen in FIG. 6, the assembled sling is worn by a postoperative patient by placing it around the back of their neck so as to be supported by the neck and shoulders in an inverted U-shaped fashion with the ends of the straps 11A, 11B hanging down along the front or sides of the patient's torso. The sling 10 can be easily adjusted, as described above, to fit any patient and strategically position the loops and drainage bulbs or receptacles supported thereby at locations adjacent to the patient's body to allow easy access and avoid tangling and stress on the drain tubes. In the example described above having four hook and loop fasteners on each loop, the sling is capable of supporting up to eight drainage bulbs on the loops, and two more bulbs may be pinned or secured to the bottom of each loop if needed. Thus, the sling is capable of supporting as many as ten or more drainage bulbs. While still having the drainage bulbs attached, the straps can be separated in the middle and easily removed from the patient's neck to relieve pressure, then re-fastened for ambulation.

While this invention has been described fully and completely with special emphasis upon a preferred embodiment, it should be understood that within the scope of the appended claims the invention may be practiced otherwise than as specifically described herein.

The invention claimed is:

1. A neck sling to be supported around the back of the neck of a postoperative patient for holding one or multiple post-surgical fluid drainage receptacles with associated drainage tubes adjacent to the body of the patient, comprising:

an elongate generally rectangular longitudinally adjustable sling formed of a first and second elongate rectangular strap of substantially the same size, each formed of a soft flexible fabric material, each said strap having opposed first and second ends and each having a pair of strips of a respective member of a mating hook and loop fastener material secured to one side thereof in longitudinally spaced relation between said first and second ends;

said first and second straps releasably secured together in opposed longitudinal overlapped relation by their respective said hook and loop fasteners engaged in face-to-face relation to provide a selected combined total length between said second ends, said straps being adjustable as to said total length;

a loop formed of a soft flexible fabric material secured to said second end of each said strap, respectively, each said loop having a plurality of strips of a first element of a hook and loop fastener material secured to one side thereof in longitudinally spaced relation and a plurality of strips of a mating second element of the hook and loop fastener material, each secured at one end to one end of a respective one of said strips of a first element of the hook and loop fastener material, so as to be unfastened by lifting one end for releasably securing one or multiple post-surgical fluid drainage receptacles to said loop; and each said mating second element of said hook and loop fastener material of said loop defining releasable fastener means for receiving a tab of a respective post-surgical fluid drainage receptacle in said unfastened lifted condition and securing the drainage receptacle on said loop in a fastened condition;

said sling adapted to be placed around the back of the neck of the postoperative patient and supported by the patient's neck and shoulders in an inverted U-shaped fashion with opposed ends of said sling hanging down along the front or sides of the patient's torso, and the one or multiple post-surgical fluid drainage receptacles attached thereto disposed at locations adjacent to the patient's body to allow easy access and avoid tangling and stress on drain tubes extending between the patient's body and the drainage receptacles.

2. A method for supporting one or multiple post-surgical fluid drainage receptacles with associated drainage tubes adjacent to the body of a postoperative patient, comprising:

providing a first and second elongate rectangular strap, each formed of a soft flexible fabric material, each said strap having a pair of strips of a respective member of a mating hook and loop fastener material secured to one side thereof in longitudinally spaced relation, and a loop formed of a soft flexible fabric material secured to one end of each said strap, respectively, each said loop having a plurality of strips of a first element of a hook and loop fastener material secured to one side thereof in longitudinally spaced relation and a plurality of strips of a mating second element of the hook and loop fastener material, each secured at one end to one end of a respective one of said strips of a first element of the hook and loop fastener material, so as to be unfastened by lifting one end;

overlapping said first and second straps with their respective said hook and loop fasteners in face-to-face relation and pressing them together to engage the fasteners to form an elongate generally rectangular sling with said loops disposed at opposed ends thereof;

lifting one end of at least one said second element of the hook and loop fastener material of at least one said loop and placing it through a tab of a post-surgical fluid drainage receptacle and thereafter pressing the lifted end onto the respective first element of the hook and loop material to releasably secure at least one drainage receptacle on at least one said loop;

placing said sling around the back of the neck of the postoperative patient so as to be supported by the patient's neck and shoulders in an inverted U-shaped fashion with the loops at opposed ends of the sling assembly hanging down along the front or sides of the patient's torso; with at least one post-surgical fluid drainage receptacles attached thereto disposed at a location adjacent to the patient's body to allow easy access and avoid tangling and stress on drain tubes extending between the patient's body and the drainage receptacle.

3. The method according to claim 2, comprising the additional step of:

lifting one end of other said second elements of the hook and loop fastener material of each said loop and placing it through a tab of a respective post-surgical fluid drainage receptacle and thereafter pressing the lifted end onto the respective first element of the hook and loop material to releasably secure multiple drainage receptacles on each said loop.

4. The method according to claim 2, comprising the additional step of:

adjusting the total length of said sling as necessary to fit different size patients by overlapping said first and second straps with their respective said hook and loop fasteners in face-to-face relation and pressing them together to engage the fasteners and releasably fasten said straps together in longitudinally spaced relation relative to one another to achieve a total length such that the at least one post-surgical fluid drainage receptacle attached thereto is disposed at a location adjacent to the patient's body to allow easy access and avoid tangling and stress on the drain tubes.

* * * * *